Figure 1:
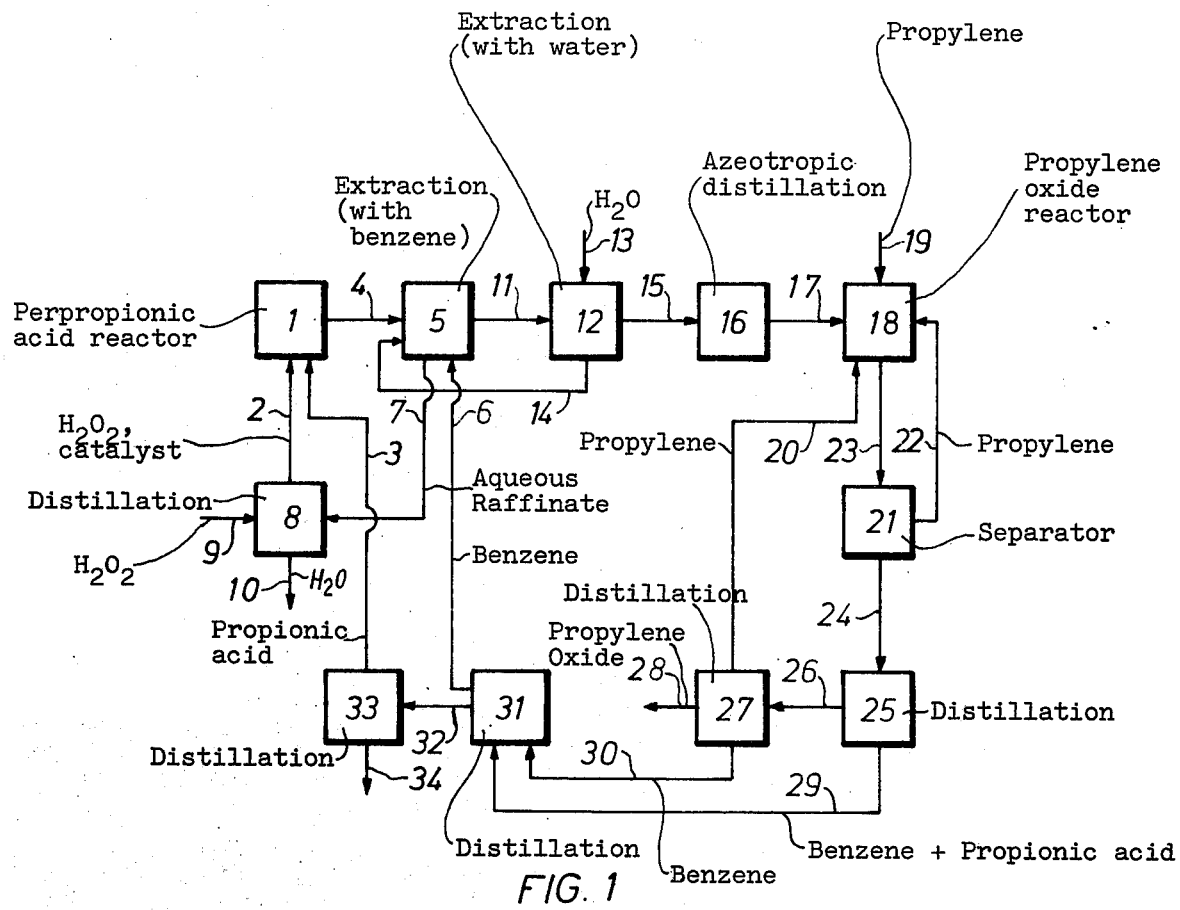

United States Patent [19]

Prescher et al.

[11] 4,113,747
[45] Sep. 12, 1978

[54] PROCESS FOR THE PREPARATION OF PROPYLENE OXIDE

[75] Inventors: Günter Prescher; Gerd Schreyer, both of Hanau; Otto Weiberg, Neu-Isenburg; Rolf Wirthwein, Hanau; Helmut Waldmann, Leverkusen; Hermann Seifert, Cologne; Wulf Schwerdtel, Leverkusen; Wolfgang Swodenk, Odenthal, all of Germany

[73] Assignees: Bayer Aktiengesellschaft, Leverkusen; Deutsche Gold- und Silber-Scheideanstalt Vormals Roessler, Frankfurt am Main, both of Germany

[21] Appl. No.: 678,822

[22] Filed: Apr. 28, 1976

[30] Foreign Application Priority Data

Apr. 30, 1975 [DE] Fed. Rep. of Germany ....... 2519298

[51] Int. Cl.² .......................................... C07D 301/14
[52] U.S. Cl. .............................. 260/348.25; 260/502 R
[58] Field of Search ................... 260/348.5 L, 502 R, 260/348.25

[56] References Cited

FOREIGN PATENT DOCUMENTS 1,917,031 10/1969 Fed. Rep. of Germany .... 260/348.5 L
2,262,970 7/1974 Fed. Rep. of Germany ...... 260/502 R
1,188,791 4/1970 United Kingdom ................... 348.5 L/

Primary Examiner—Norma S. Milestone
Attorney, Agent, or Firm—Burgess, Dinklage & Sprung

[57] ABSTRACT

Process for continuous production of propylene oxide (FIG. 1) from propylene and aqueous hydrogen peroxide. The aqueous hydrogen peroxide is first reacted with propionic acid in the presence of acid catalyst to form perpropionic acid (1). The perpropionic acid is taken up by extraction in benzene (5, 12), and following drying of the benzene solution (16), the perpropionic acid in the solution is reacted with propylene (18) for oxidation of the propylene to propylene oxide and conversion of the perpropionic acid back to propionic acid. The reaction mixture is worked up to separate propylene oxide, propionic acid and benzene (25, 27, 31, 33), and the latter two are recycled. In the benzene extraction (5, 12), an aqueous raffinate (7) is formed containing hydrogen peroxide and acid catalyst. Water is removed from the aqueous raffinate (8) and the concentrate is recycled to the propionic acid reactor. Make-up hydrogen peroxide can be added to the aqueous raffinate before the removal of water.

32 Claims, 4 Drawing Figures

PROCESS FOR THE PREPARATION OF PROPYLENE OXIDE

The following applications are related to the process hereof for production of propylene oxide as being directed to aspects of the process, some of which are disclosed herein.

| German Serial No. | U.S. Serial No. |
|---|---|
| P 25 19 288.5 | 678,819 |
| P 25 19 300.4 | 678,820 |
| P 25 19 299.8 | 678,821 |
| P 25 19 297.6 | 678,823 |
| P 25 19 295.4 | 678,824 |
| P 25 19 293.2-42 | 678,825 |
| P 25 19 292.1-42 | 678,826 |
| P 25 19 291.0-42 | 678,827 |
| P 25 19 289.6 | 678,828 |
| P 25 19 297.4 | 678,829 |

All of said related applications were filed on Apr. 28, 1976.

The present invention relates to a continuous process for the industrial production of propylene oxide from hydrogen peroxide and propylene.

Hitherto propylene oxide has been prepared on a large industrial scale by two processes exclusively, that is either according to the older process via propylene chlorohydrin or more recently with the aid of hydrocarbon peroxides.

The older chlorohydrin process has the disadvantage that undesirable chlorinated by-products and waste salts which pollute the environment are formed (DAS (German published specification) No. 1,543,174, column 2, lines 15 et seq.).

The more recent process, used industrially, for the preparation of propylene oxide via hydrocarbon peroxides, such as described, for example, in USA Patent Specification 3,350,422, eliminates these considerable disadvantages of the chlorohydrin process. The reaction of propylene with a hydrocarbon peroxide ROOH can be illustrated by the equation (1).

It can be seen from equation (1) that in this reaction 1 mol of the alcohol ROH corresponding to the peroxide is always formed per 1 mol of propylene oxide formed. The hydrocarbon peroxide thus effects a transfer of oxygen so that, after the release of the peroxide oxygen, the corresponding alcohol is obtained as a co-product and frequently has to be removed as an undesired by-product. Accordingly, the possibilities for industrial use of such a process are limited, since the alcohol by-product cannot be utilised in every case.

In contrast, with the principle on which the process according to the invention for the preparation of propylene oxide from propylene and hydrogen peroxide is based, the desired end product is obtained, as is shown in equation (2), free from such by-products, which either have to be eliminated at considerable expense because of their environmental pollution properties or for which a suitable further use has to be found when they are obtained as co-products.

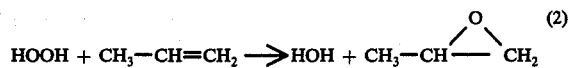

However, the desired objective is not achieved by direct reaction of propylene with aqueous hydrogen peroxide (U.S. Pat. specification No. 3,350,422, column 2, lines 42–44).

On the other hand, it is known to epoxidise propylene with the aid of a percarboxylic acid to give propylene oxide (Prileschayev, Ber, dtsch. chem. Ges. 42, 4811 (1909) and D. Swern "Organic Peroxides", Wiley Interscience 1971, volume 2, page 355–533, especially page 375–378 and page 397). In addition, it is known to obtain percarboxylic acids from carboxylic acids with the aid of hydrogen peroxide (German Pat. No. 251,802 and, for example, D. Swern, loc. cit., 1970, volume 1, page 313–369 and page 428–439). These two partial steps are illustrated in the equations (3) and (4), in which R—COOH and R—COOOH represent a carboxylic acid and a percarboxylic acid respectively.

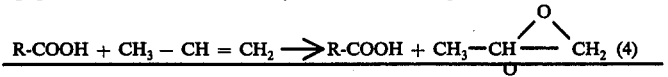

If the carboxylic acid obtained according to equation (4) is recycled into the reaction according to equation (3) to obtain percarboxylic acid, the overall equation (2) results for the reaction of hydrogen peroxide with propylene to give propylene oxide. A process of this type for the preparation of propylene oxide starting from hydrogen peroxide and propylene and using percarboxylic acids as the epoxidising agent has not hitherto been mastered in an industrially satisfactory manner and consequently has not yet been used on an industrial scale. In this connection it is stated, for example in U.S. Pat. No. 3,350,422 (column 1, line 65 to column 2, line 11):

"In light of the complexity and cost of the chlorohydrin route, workers have turned to other possible routes for the epoxidation of propylene and other olefins. One route which has proved successful insofar as being capable of actually producing at least limited yields of propylene oxide and other oxides is the peracid route. This route involves the formation of a peracid, such as peracetic acid, through the reaction of hydrogen peroxide with the organic acid and the epoxidation of an olefin with the peracid. The disadvantages of the peracid route also are such as to preclude significant commercialization. The peracids themselves are extremely hazardous to handle and give rise to severe operation problems. The reagents are expensive, corrosive, and nonregenerable, inasmuch as the hydrogen peroxide is lost as water. The composition of the peracid epoxidation mixture contains chemicals ($H_2O$, AcOH, and $H_2SO_4$) which are highly reactive with the product epoxides, thus leading to many by-products (glycol, glycol monoester, glycol diester) which lower the overall efficiency. This problem becomes more severe with the less reactive olefins, in particular propylene".

In fact, all the processes hitherto known for the preparation of propylene oxide from hydrogen peroxide and propylene, which proceed via the intermediate stage of a percarboxylic acid as an oxygen transfer agent, lead only to unsatisfactory yields of propylene oxide and to considerable amounts of by-products, such as propylene glycol, propylene glycol monoester and propylene glycol diester. It has also not been possible satisfactorily to overcome the extremely difficult process problems, especially with regard to the isolation of the percarboxylic acid, which are caused by the explosion hazard of the percarboxylic acids.

In the case of the process according to DOS (German published specification) No. 1,618,625, which has been disclosed more recently, for the preparation of oxiranes from olefines and hydrogen peroxide with the aid of formic acid, the measures described there are also not adequate for an industrially satisfactory production of propylene oxide from hydrogen peroxide and propylene. For this process it is necessary for the reaction mixture to be substantially free from mineral acid and substantially anhydrous or to contain only a small amount of water (DOS (German published specification) No. 1,618,625, claim 1). Thus, it is stated, for example, on page 3, final paragraph and page 4, first line of DOS (German published specification) No. 1,618,625: "The use of an anhydrous reaction mixture is desired, but the preparation of solutions of performic acid having less than about 0.3% of water is neither simple nor economically tenable. The use of a reaction mixture which contains only a small amount of water is preferred." An amount of less than 20 g/l is mentioned as an appropriate water content and an amount of less than 10 g/l is mentioned as being a required water content in some cases. The freedom from mineral acid, which it is attempted to achieve in the process, is important since the catalysts required for the reaction of formic acid with hydrogen peroxide also catalyse the cleavage reaction of oxirane rings, in the present case the cleavage of propylene oxide (DOS (German published specification) No. 1,618,625, page 5, lines 10–14). Accordingly, it would be most advantageous to use in the process a solution, which as far as possible is absolutely anhydrous and as far as possible is free from mineral acid, of performic acid in a hydrophobic solvent. These requirements, particularly with regard to the freedom from water, cannot be met in the processes known hitherto, since the preparation of a non-aqueous performic acid containing only 0.3% of water or less already comes up against the difficulties mentioned in DOS (German published specification) No. 1,618,625. Accordingly, the yield of propylene oxide which can be achieved, for example, according to the process of DOS (German published specification) No. 1,618,625, is only 85%, relative to the performic acid consumed (DOS (German published specification) No. 1,618,625, Example 3). However, since the performic acid solutions still have a relatively high content of free hydrogen peroxide, this being between 3 and 10 mol % of the performic acid according to Examples 1 and 2 of DOS (German published specification) No. 1,618,625, the yield of propyleene oxide, relative to hydrogen peroxide employed, is even lower, since the hydrogen peroxide contained in the performic acid solution used as the epoxidising agent can not be recovered from the mixtures, containing propylene oxide, which are obtainable from the reaction with propylene. It is not possible to determine the accurate percentage figures for the final yield of propylene oxide, relative to hydrogen peroxide employed, from the data given in the examples; however, it is less than 50%.

A further disadvantage of the process of DOS (German published specification) No. 1,618,625 is that the formic acid used as the oxygen transfer agent is a special case amongst the carboxylic acids with regard to the question of corrosion also, which is always of considerable importance in reactions with lower carboxylic acids, because formic acid is even particularly corrosive towards stainless steels. It is precisely in a process in which sensitive peroxy compounds, such as hydrogen peroxide and percarboxylic acids, are used that corrosion of any type is extremely undesirable since, due to corrosion, heavy metal compounds which cause the decomposition of hydrogen peroxide and of the percarboxylic acid are carried into the reaction.

In another more recent process for the preparation of olefine oxides from olefine and hydrogen peroxide,, an aromatic carboxylic acid, preferably benzoic acid, is used as the oxygen transfer agent (DOS (German published specification) No. 2,312,281). However, in this process the problem of obtaining the percarboxylic acid by reaction of hydrogen peroxide with an aromatic carboxylic acid has not been solved satisfactorily. That is to say, the reaction mixture, containing percarboxylic acid, which is obtainable must be diluted, for further working up, with ice water and cooled ammonium sulphate solution whilst maintaining a temperature of less than 25° C and the unreacted hydrogen peroxide is then destroyed. (DOS (German published specification) No. 2,312,281, page 5, 2nd and 3rd paragraph). A further disadvantage of this process is that the rate of reaction of the aromatic percarboxylic acid with propylene is very low, since after a reaction time of 4 hours at a temperature of 28° to 30° C only 66% of the percarboxylic acid are converted. The total yield of propylene oxide, relative to hydrogen peroxide employed, is apparently very small with this process. According to Example 1 of DOS (German published specification) No. 2,312,261, the final yield for propylene oxide, relative to hydrogen peroxide employed, is about 40%.

A further process which can be used to prepare propylene oxide is the process for the oxidation of propylene described in DOS (German published specification) No. 1,917,031, in which propylene is reacted with an equilibrium mixture consisting of at least one carboxylic acid, hydrogen peroxide and water, in the absence of mineral acid and heavy metal ions, the amount of water present during the reaction being so regulated that at least one compound from the group comprising propylene oxide, propylene glycol and propylene glycol esters is obtained. When carrying out the process in practice, a hydrogen peroxide solution prepared by air oxidation of a secondary alcohol, for example isopropanol, is used as the starting material for the preparation of the equilibrium mixture to be employed in the process and is treated with a urea solution in order to form a urea/hydrogen peroxide adduct, which is mixed with an extracting solvent (an alkyl ketone, alkyl ester or alkyl ortho-phosphate), by which means the hydrogen peroxide is dissolved in the extracting solvent, urea being deposited, and subsequently at least part of the extracting solvent in the resulting hydrogen peroxide solution is mixed with the carboxylic acid, for example acetic acid, or replaced by this (DOS (German published specification) No. 1,917,031, page 3 and also Example 1). The oxidation of propylene then carried out using the equilibrium mixture leads to the formation of propylene oxide, propylene glycol and propylene glycol esters in varying amounts (loc. cit., page 4, lines 2 and 3). The ratio of propylene oxide to propylene glycol and propylene glycol esters is regulated by the amount of water and excess carboxylic acid which remains in the equilibrium mixture containing the percarboxylic acid (loc. cit., page 5, lines 6–8). When the process is intended to give propylene oxide as the main product, it is appropriately carried out, as can be seen from DOS (German published specification) No. 1,917,031, using only a slight excess of carboxylic acid, since, as is known, the presence of larger amounts of carboxylic acid easily leads to the formation of propylene glycol and the esters thereof and not to the formation of propylene oxide (loc. cit., page 6, lines 18 to 23). This in turn means that the rate of formation of the percarboxylic acid is reduced and this has an adverse effect on the economics of the process (loc. cit., page 7, line 1 to 4). Moreover, because of the absence of mineral acid, the rate of formation of the percarboxylic acid in this process is considerably lower at all molar ratios of hydrogen peroxide to carboxylic acid than when mineral acid is present. The effect of this is, of course, very particularly disadvantageous if the excess of carboxylic acid is small. The yields of propylene oxide, relative to hydrogen peroxide employed, achieved according to this process are small, especially because the unreacted hydrogen peroxide is not recovered and the unreacted percarboxylic acid is destroyed. Because of the lack of data, the yields of propylene oxide, relative to hydrogen peroxide employed, cannot be calculated accurately from the two illustrative examples of DOS (German published specification) No. 1,917,031. However, it can clearly be seen from the data of DOS (German published specification) No. 1,917,031 that the peracetic acid solution prepared according to Example 1(a) must still have contained substantial amounts of free hydrogen peroxide, so that the yield of peracetic acid, relative to the amount of hydrogen peroxide employed, can have been about 69% in the most advantageous case. Accordingly, the yield of propylene oxide, relative to hydrogen peroxide employed, of course also falls considerably, to about 64% in Example 2(b,i).

Accordingly, it can be seen from the state of the art that it has not been possible to find a technically satisfactory solution, not only in respect of the process step for the preparation of the percarboxylic acid, but in particular also in respect to the subsequent reaction of the percarboxylic acid, for example as a non-aqueous solution, with propylene to give propylene oxide. Improvements in this reaction with regard to process engineering, such as have been described in British patent specification No. 1,105,261, German patent specification No. 1,216,306 and DOS (German published specification) No. 1,923,392, also have such great disadvantages that they cannot be used for carrying out the process on an industrial scale.

The basic assumption in British patent specification No. 1,105,261 is that only yields of 75%, relative to the percarboxylic acid, are possible when this reaction is carried out by mixing the reactants, for example by mixing propylene and peracetic acid (British patent specification No. 1,105,261, page 1, lines 20–24).

Not it is proposed in British patent specification No. 1,105,261 to use a series of closed reaction loops, in which mixing of reaction products with the starting substances is largely prevented, for carrying out the reaction of a non-aqueous peracetic acid solution with propylene. However, the proposed is not adequate for an economical preparation of propylene oxide from propylene and a percarboxylic acid, since the yield of propylene oxide, relative to peracetic acid amployed, is only 90% and 2.5 mols % of propylene glycol monoacetate and a further 2.5 mol % of other higher boiling by-products are formed (British patent specification No. 1,105,261, page 3, lines 60–68).

Even according to the process of German patent specification No. 1,216,306, by using coiled tubes of very precise dimensions for the reaction of propylene with peracetic acid, a yield of only 86% of theory is achieved. (German patent specification No. 1,216,306, column 8, line 33).

The process according to DOS (German published specification) No. 1,923,392 is intended to improve the rate of reaction and, at the same time, to prevent side reactions and secondary reactions, because, although the rate of reaction can be increased by simply carrying out the reaction under pressure, it has not been possible to prevent the occurrence of side reactions in this way (DOS (German published specification) No. 1,923,392, page 2, lines 14–18). According to the process of DOS (German published specification) No. 1,923,392, an attempt is then made to eliminate these disadvantages by using a reaction system consisting of a multiplicity of reaction zones (in practice a multi-stage bubble column). However, carrying out the reaction in this way means that, due to the requisite technically highly expensive procedure, a new and considerable disadvantage has to be accepted, because the process technology for the reaction of propylene with peracetic acid in heterogeneous phase (gaseous/liquid) is far more complicated than that for a reaction in homogeneous phase.

The Invention

In contrast, it has now been found that, starting from aqueous hydrogen peroxide and propylene, propylene oxide can be prepared continuously in a manner which is advantageous from both the technical and economic point of view when (a) an aqueous solution containing 15 to 45% by weight of a water-soluble acid catalyst and 25 to 35% by weight of hydrogen peroxide is reacted with propionic acid in a molar ratio of hydrogen peroxide:propionic acid of 0.8–1.5 : 1 at temperatures of from 10° to 70° C, (b) the resulting reaction mixture is extracted with benzene in counter-current, (c) the aqueous raffinate from the extraction, which contains in the main hydrogen peroxide and acid catalyst, is reconcentrated by removing water by e.g. distillation, (d) the reconcentrated raffinate is recycled into the reaction stage (a), the concentrations of hydrogen peroxide and acid catalyst being made up to those required for the reaction with propionic acid, by reconcentrating the aqueous raffinate according to (c) together with all or part of the hydrogen peroxide required to restore the hydrogen peroxide concentration, (e) the benzene extract, which contains in the main perpropionic acid and propionic acid, is treated with water or an aqueous solution, (f) the water-containing benzene extract, which is not virtually free from hydrogen peroxide, is subjected to an azeotropic distillation so that the residual water content in the sump of the azeotrope column is less than 0.5% by weight, (g) the solution, containing perpropionic acid and propionic acid, which is now obtained as the sump product from the azeotropic distillation, is reacted with excess propylene at temperatures of from 40° to 100° C and at a pressure of from 2 to 30, bars, and (h) the reaction mixture, containing propylene oxide, is worked up in a manner which is in itself known, pure propylene oxide being isolated and the excess propylene which may be present, the propionic acid and the benzene being recovered and the whole or part of these recovered products being recycled into the process.

Step (a) — Production of Perpropionic Acid

In the reaction according to (a) of hydrogen peroxide with propinoic acid in the presence of an acid catalyst, an equilibrium is set up between propionic acid and perpropionic acid which can be represented by the following equation:

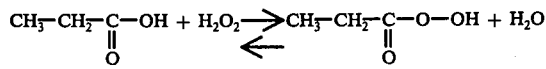

Depending on the concentration of acid catalyst, for example sulphuric acid, and hydrogen peroxide and depending on the molar ratio of hydrogen peroxide to propionic acid, about 30 to 70% of the propionic acid is converted to perpropionic acid.

In general, together with the aqueous solution containing 15 to 45% by weight of water-soluble acid catalyst, for example sulphuric acid or methanesulphonic acid, and 25 to 35% by weight of hydrogen peroxide, the propionic acid is used in the pure, undiluted form. However, it is also possible to use a propionic acid which contains water, hydrogen peroxide or an acid catalyst, it being necessary in this case to change the concentration of the aqueous solution accordingly in order to maintain the ratio of hydrogen peroxide, acid catalyst, propionic acid and water required for the reaction. Thus, for example, a mixture of propionic acid and hydrogen peroxide, for example a propionic acid containing 20% by weight of hydrogen peroxide, can be employed in place of pure propionic acid. Of course, the hydrogen peroxide content in the aqueous feed solution containing acid catalyst and hydrogen peroxide must then be adjusted according to the hydrogen peroxide content in the propionic acid, so that a total feed of hydrogen peroxide which corresponds to a hydrogen peroxide content of 25 to 35% by weight in the aqueous solution results from the hydrogen peroxide contained in the propionic acid and from that in the aqueous solution. For example, in such a case, the hydrogen peroxide content in the aqueous solution itself can be less than 25% by weight, for example 17 to 24% by weight. Within the indicated concentration ratios of catalyst and hydrogen peroxide, it is possible to use all conceivable mixing ratios. Preferably, an aqueous solution containing 30 to 45, preferentially 32 to 43,% by weight of acid catalyst and 28 to 32% by weight of hydrogen peroxide is used in the reaction. Particularly preferantially, it is also possible to use an aqueous solution containing 34 to 39% by weight of acid catalyst and 28 to 32% by weight of hydrogen peroxide.

In general, the reaction vessel is charged uniformly with the propionic acid and the aqueous solution of acid catalyst and hydrogen peroxide. However, it is also possible initially to introduce all or part of the propionic acid and to add the solution containing hydrogen peroxide.

The ratio of hydrogen peroxide to propionic acid is preferably to be so selected that the molar ratio of hydrogen peroxide to propionic acid is 0.9 to 1.3 : 1. It is particularly advantageous to use a molar ratio of 0.95 to 1.1 : 1.

Sulphuric acid is advantageously used as the water-soluble acid catalyst. Other water-soluble acids can also be used, for example sulphonic acids, such as methanesulphonic acid, ethanesulphonic acid, propanesulphonic acid, butanesulphonic acid, isobutanesulphonic acid, benzenesulphonic acid, toluenesulphonic acid, trifluoromethanesulphonic acid, 1-fluoroethanesulphonic acid, perfluorethanesulphonic acid, perfluoropropanesulphonic acid or perfluorobutanesulphonic acid; phosphoric acid, phosphonic acids, such as methanephosphonic acid or ethanephosphonic acid, phosphinic acids or acid salts such as sodium bisulphate or potassium bisulphate. Mixtures of water-soluble acids can be used. Commercially available hydrogen peroxide, for example 30 to 90% strength by weight $H_2O_2$, is used as the hydrogen peroxide to prepare the aqueous solution. Of course, hydrogen peroxide which is obtained as a by-product from other chemical processes or as a return stream is also suitable. Acids of sulfur and phosphorus are preferred.

The reaction temperature is generally between 10° and 70° C. Appropriately, the reaction is carried out at 20°-60° C. Temperatures below 45° C are particularly advantageous for the reaction. It is very particularly appropriate to maintain reaction temperatures of from 30° to 40° C.

In general, the reaction is carried on until the equilibrium between perpropionic acid and propionic acid is set up. However, it is also possible to discontinue the reaction before the equilibrium is reached and to feed the reaction mixture thus obtained to the next process stage, that is to say the extraction with benzene.

The pressure is not important for the reaction of propionic acid with hydrogen peroxide, so that the reaction can be carried out at normal pressure, elevated pressures or at reduced pressure. In general it is appropriate to carry out the reaction at pressures below 1.1 bars.

The reaction can be carried out in very diverse reaction vessels. It is appropriate to make provision for a steady state concentration profile and in particular to avoid so-called pockets in which parts of the reaction mixture remain for a disproportionately long time. Suitable vessels are, for example, the customary reaction tubes of varying diameter and varying length, which can also be arranged as a closed cycle, for example as loop reactors, as well as stirred kettles.

Step (b) — Benzene Extraction

The reaction mixture from reaction stage (a) is now fed to the counter-current extraction with benzene according to (b). In addition to benzene, other solvents which are immiscible with water and which are inert towards the reaction mixture from reaction (a), for example hydrocarbons, such as toluene, xylene, ethyl-benzene or cyclohexane; chlorinated hydrocarbons, such as methylene chloride, 1,2-dichloroethane, 1,2-dichloropropane or 1,2-dichloro-1,2-difluoroethane; esters, such as ethyl acetate, ethyl propionate, phosphoric acid tributyl ester, phosphoric acid triisooctyl ester or methanephosphonic acid octyl ester, or ethers, such as di-(4-chlorobutyl) ether, are also suitable. For example, circulating benzene which contains less than 0.5%, preferably less than 0.1% of propionic acid is used. The volume ratio of benzene to the reaction mixture to be extracted is generally 3 to 0.3 : 1. However, larger amounts of benzene can also be used.

The perpropionic acid content in the extract can be varied within wide limits by the amount of the extraction agent and by the number of extraction stages. In general, the procedure is such that an approximately 5 to 30% strength by weight solution of perpropionic acid in benzene is obtained. Preferably, a benzene extract containing about 15 to 25% by weight of perpropionic acid is produced. Accordingly, the number of extraction stages should be as large as possible. However, in general an extraction unit with 5 to 10 theoretical extraction stages is adequate in order to prepare the solutions with the desired concentration of perpropionic acid. Of course, it is desirable to obtain the raffinate as free as possible from propionic acid and perpropionic acid. However, it is generally adequate if not more than 0.2% of propionic acid and perpropionic acid remains in the raffinate.

The temperature during the extraction can be varied within wide limits. In general, the extraction is carried out at temperatures of from 10° to 70° C. Appropriately, the temperature selected is the same as that used for the reaction to obtain perpropionic acid according to (a), so that the other temperatures mentioned for reaction step (a) are also possible for the extraction (b). With regard to the pressure, the extraction can be carried out at normal pressure, reduced pressure or at elevated pressures.

Extraction units which can be used are the known extraction systems with which multi-stage counter-current extraction is possible. For example, mixer/settlers, sieve tray extractors, pulsed sieve tray columns or spray columns are suitable. However, single-stage or multi-stage centrifugal extractors can also be used.

In addition to perpropionic acid and propionic acid, the organic extract still contains small amounts of free hydrogen peroxide, water and traces of the acid used as the catalyst, for example sulphuric acid. The raffinate essentially contains the unreacted hydrogen peroxide and the acid catalyst.

Steps (c) and (d) — Recovery of $H_2O_2$ and acid from aqueous phase

The raffinate, containing in the main hydrogen peroxide and, for example, sulphuric acid, is now worked up in process step (c) for further reaction of propionic acid and hydrogen peroxide by treating it with that amount of fresh aqueous hydrogen peroxide which is consumed in the course of the process and by reconcentrating the resulting mixture by removing water in a distillation, so that an aqueous solution which contains the amounts of sulphuric acid and hydrogen peroxide indicated for process step (a) is obtained as the sump product. Water, which can contain small amounts of hydrogen peroxide, perpropionic acid and propionic acid, is obtained as the top product from the distillation. In general, the distillation is best carried out under reduced pressure, for example at pressures of from 10 to 250 mm Hg, preferably 50 to 150 mm Hg, and at temperatures in the sump of from 40 to 120° C, preferably from 60° to 85° C.

The fresh hydrogen peroxide for replenishing the amounts consumed can be added in any desired concentration. It is appropriate to use a commercially available hydrogen peroxide, for example 30 to 90% strength by weight aqueous hydrogen peroxide, to which the customary stabilisers can be added. For example, stabilisers such as are mentioned in Gmelins "Handbuch der anorganischen Chemie" ("Handbook of Inorganic Chemistry"), 8th edition, oxygen volume, section 7, 1966, on page 2274 and page 2275, are suitable.

The fresh hydrogen peroxide can be mixed, prior to entry into the distillation unit, with the raffinate from the extraction according to process stage (b); the two mass flows can also be fed separately into the distillation unit.

It is likewise possible to add the fresh hydrogen peroxide e.g. partly to the aqueous raffinate of the extraction after concentration according to (c).

Thus, a substantial part of the fresh hydrogen peroxide, which is required in the process, e.g. 50% by weight of this amount, can be added to the raffinate prior to the removal of water by distillation and the remaining 50% by weight of the fresh hydrogen peroxide added to the concentrated raffinate stream.

The process is preferably carried out in such a manner that 50 to 75% by weight of the fresh hydrogen peroxide is added to the raffinate of the extraction prior to concentration, whilst the remaining 25 to 50% by weight of the amount of the fresh hydrogen peroxide needed in the process is added to the raffinate after concentration. It is possible to mix the part of fresh hydrogen peroxide to be added prior to the raffinate concentration with the raffinate before entry into the distillation unit or to introduce both streams separately at a suitable place into the distillation unit. The amount of fresh hydrogen peroxide, which is added to the raffinate not prior to concentration, can also be introduced directly into the reaction with propionic acid according to (a).

In this case, as in the case of the addition of a part of the fresh hydrogen peroxide to the concentrated raffinate, the concentrations of $H_2O_2$ and acid catalyst must be correspondingly altered in the concentrated raffinate (in so far as the partial streams of fresh hydrogen peroxide which are used in the process as aqueous solutions have the same concentrations).

This alteration to the concentrate must be carried out in order that the required amount ratio of $H_2O_2$, acid catalyst and water be provided for the reaction with propionic acid. This is expediently carried out in such a manner that the amount of water, which is introduced into the process with the partial stream of the fresh hydrogen peroxide added to the raffinate after concentration or directly to the reaction with propionic acid is removed by distillation. This is preferably achieved in the distillation unit used for the concentration of the raffinate.

It is also possible, however, to introduce partial streams of fresh hydrogen peroxide into the process which have a varying concentration of $H_2O_2$. Thus, it is possible, for example, to add 70% by weight of the required amount of fresh hydrogen peroxide to the raffinate of the extraction prior to concentration in the form of a 50% by weight aqueous solution, whilst the remaining 30% by weight of fresh hydrogen peroxide are introduced as a more highly concentrated aqueous solution of $H_2O_2$, for example, as a 70% by weight solution.

In a preferred embodiment of the process, the process is carried in such a way that the amount of fresh $H_2O_2$, which is added to the raffinate of the extraction prior to removal of water by distillation, amounts to 75 to 95% by weight of the total amount of fresh hydrogen peroxide and that the remaining 5 to 25% by weight of fresh $H_2O_2$ is added to the concentrated raffinate. In a particularly preferred embodiment, the process is so performed that the fresh hydrogen peroxide is introduced by adding the total amount to the raffinate of the extraction prior to concentration in a distillation unit.

Appropriately, a column provided with a condenser and an evaporator unit is used as the distillation unit. The known trayed columns or packed columns can be used for the distillation. The number of distillation stages is so selected that the top product contains as little hydrogen peroxide as possible. It is desirable to obtain less than 0.1% by weight of hydrogen peroxide in the condensate. In principle, the known evaporators are suitable as the evaporator unit. For example, those evaporator units in which the residence time of the product is less than 20 minutes, preferably less than 10 minutes, are suitable. Falling flow evaporators or thin layer evaporators are particularly suitable. Suitable materials for the distillation unit are high-alloy, high grade stainless steels which, in addition to iron, also contain in the main chromium and nickel, such as, for example, a material with the DIN designation 1.4571, which, in addition to iron contains 17.5% by weight of chromium, 11.5% by weight of nickel, 2.25% by weight of molybdenum and up to 2% by weight of manganese, up to 1% by weight of silicon, up to 0.1% by weight of carbon and small amounts of titanium, or a material which, in addition to iron, contains 25% by weight of chromium, 25% by weight of nickel, 2.25% by weight of molybdenum and up to 2% by weight of manganese, up to 1% by weight of silicon, up to 0.06% by weight of carbon and also small amounts of titanium and which is designted according to DIN by the number 1.4577. Zirconium, materials containing zirconium and zirconium alloys are particularly suitable as the material for the distillation unit, especially for the evaporator.

The sump product from this distillation unit is fed back into the reaction stage (a), the concentrations of hydrogen peroxide and the catalyst being restored, as appropriate, to those required for the reaction with propionic acid. In this way it is possible to recycle the unreacted hydrogen peroxide and the acid catalyst virtually without loss, so that hydrogen peroxide can be completely converted and the catalyst, for example the sulphuric acid, can be used again and again. By virtue of this procedure a circulation of hydrogen peroxide and catalyst is obtained. It can be appropriate to remove part, for example 0.1 to 6% by weight, of the circulating flow from the process from time to time or continuously. In principle, a sidestream of this type can be withdrawn at any desired point in the circulation, of hydrogen peroxide and acid catalyst, which essentially comprises the process stages (a), (b), (c) and (d). Appropriately it is withdrawn from the raffinate of the extraction according to (b). This sidestream can either be discarded or can be fed into a regeneration stage for working up. For example, regeneration can be effected by distilling off the hydrogen peroxide in vacuo with steam, an aqueous solution of the acid catalyst being obtained as the distillation residue. The aqueous solution, containing hydrogen peroxide, obtained as the distillate can be fed back into the process, if appropriate after reconcentration. After purification, for example by distillation, the aqueous solution of the acid catalyst can also be fed back into the process. By means of this exchange in the circulation, a corresponding part of the catalyst, for example the sulphuric acid, is lost and thus has to be replenished in the process. It is appropriate to replenish the sulphuric acid by adding the required amount of $H_2SO_4$ in the form of a mixture of sulphuric acid and aqueous hydrogen peroxide.

Step (e) — Water Treatment of Benzene Extract

The benzene extract which essentially contains perpropionic acid and propionic acid and which is obtained according to process stage (b) is treated in process step (e) with water or an aqueous solution. In general the procedure is such that the benzene extract containing perpropionic acid is washed with water in one of the devices customary for this purpose.

It is appropriate to carry out this washing as an extraction, for example as a multi-stage counter-current extraction, with water, for example in a three-stage extraction unit. Of course, a co-current extraction or crosscurrent extraction can also be used in place of countercurrent extraction. When working with several extraction stages, the extraction can also be carried out partially as co-current extraction and partially as counter-current extraction.

Appropriately, 1 to 10% by volume of water or aqueous solution, relative to the benzene extract, is used. Preferably, 3 to 6% by volume of water are used. In place of pure water, it is also possible to use an aqueous solution which is substantially free from hydrogen peroxide and from mineral acid. It is appropriate to use an aqueous phase which is obtained in the process. For example, the aqueous phase from the azeotropic distillation according to (f) is suitable. The aqueous phase from the water treatment can be fed back into the extraction with benzene according to (b) in order to obtain for the process the amounts of perpropionic acid and hydrogen peroxide contained therein.

The known extraction systems, for example mixer/settlers, sieve tray extractors, pulsed sieve tray columns or extraction centrifuges, are suitable as equipment for the water treatment according to process stage (e).

Step (f) — The Aceotropic Distillation

In this way, a benzene solution which contains perpropionic acid and which is substantially free from hydrogen peroxide and from sulphuric acid is obtained and is then subjected to azeotropic distillation according to process stage (f). In this stage the water contained in the benzene solution of perpropionic acid is removed. In general, the amount of distillate is so selected that the residual water content in the sump of the azeotrope column is less than 0.5% by weight, preferably less than 0.2% by weight. However, it is also possible to reduce the water content to a negligibly small value. The benzene which separates off as the organic phase after condensation of the top vapours from the azeotrope column is returned as reflux to the column. The aqueous phase which is obtained after condensation of the top vapours and which generally contains small amounts of perpropionic acid, propionic acid and also hydrogen peroxide, is fed back into the process at a suitable point, for example at the extraction according to (e) or (b); however, it can also be withdrawn from the process.

The azeotropic distillation (f) can be carried out at normal or reduced pressure, for example 30° to 80° C. In general, a sump temperature of below 70° C is adequate.

The customary columns, for example the known trayed or packed columns, are suitable for the azeotropic distillation. The customary equipment can be used as the evaporator. Falling flow evaporators or thin layer evaporators are preferred suitable equipment.

Step (g) — The Oxidation of Propylene Oxide

The solution, which is thus obtained as the sump produce from the azeotropic distillation, of a perpropionic acid which is substantially anhydrous and free from hydrogen peroxide, in benzene is reacted in process step (g) with an excess of propylene, for example in a molar ratio of propylene: perpropionic acid of 1.01 to 8 : 1, at temperatures of from 40° to 100° C and at pressures of from 2 to 30 bars. The reaction can also be carried out at a pressure of from 2.5 to 20 bars. Pressures of from 4 to 18 bars, for example, constitute a suitable pressure range. Preferably, the reaction is carried out at a pressure of from 6 to 14 bars. The reaction temperature is preferably kept at 60°-80° C. In addition to the procedure under isothermal conditions, that is to say maintaining a uniform temperature in the entire reaction mixture, a procedure is also possible with which a so-called temperature gradient, which generally increases as the reaction progresses, is set up. However, the reaction can also be carried out in such a way that a falling temperature gradient is set up as the reaction progresses.

Appropriately, the pressure when carrying out process step (g) is so selected that the reaction mixture is in the main present in the liquid phase. At a molar ratio of propylene : perpropionic acid of, for example, 2.5 : 1 and at a reaction temperature of 65° to 75° C, the pressure is, for example, 10 to 12 bars.

The molar ratio of propylene to perpropionic acid is preferably 1.5 to 4 : 1. It is very particularly advantageous to use a molar ratio of 2.0 to 3.0 mols of propylene per mol of perpropionic acid.

The equipment customary for reactions of this type, such as stirred kettles, tube reactors, loop reactors or looped reactors, can be used for carrying out the reaction. In general, equipment is used which acts as a cascade of at least two ideally mixed kettles. It is particularly advantageous to use a reaction system which acts as a cascade of 4 to 50, preferably 10 to 30, ideally mixed kettles. When actually carrying out the reaction, for example, a train of several stirred kettles, for example a cascade of from 3 to 6 kettle reactors, is used.

In general, technical grade propylene is used for the reaction according to the process step (g). It can contain the impurities customary in industrial use, in particular propane. Of course, specially purified propylene, for example propylene containing less than 0.5% of propane, can also be used.

The propylene can be introduced into the reaction unit in different ways. The propylene can be employed in the liquid or gaseous form. The propylene can also be passed together with the perpropionic acid solution into the reactor unit. The two feed materials can also be introduced into the reactor separately from one another. It is further possible to pass the propylene and the perpropionic acid solution into the reactor unit at different points. When using several reactors arranged in a cascade, it can be appropriate to introduce all of the propylene into the first reactor. However, the propylene can also be divided between the various reactors.

The considerable heat of reaction is removed by internal and external coolers. In order to remove the heat of reaction, the reaction can also be carried out under reflux (boiling reactors). Approriately, the reaction is carried out with as complete as possible a conversion of the perpropionic acid. In general, more than 98% of the perpropionic acid is converted. It is appropriate to convert more than 99% of the perpropionic acid. The reaction can be carried out with a particularly high selectivity if it is carried out partially in a reaction tube in which there is turbulent flow, the reaction tube connected, for example, to the train of stirred kettles. It is particularly advantageous to use a reaction tube which is provided with inserts which largely prevent back-mixing, for example perforated baffle plates. For example, the reaction is carried out first in several, for example 1 to 3, stirred reaction units arranged in series and the reaction mixture is then passed into a reaction tube in order to complete the reaction. The reaction tube can be operated under adiabatic conditions; however, it is also possible to cool, for example by means of external cooling, or to fit coolers between individual sections of the tube. The dimensions of a suitable reaction tube depend on the intended throughput. It is essential that the flow velocity in the reaction tube is so high that back-mixing of the reaction components is substantially excluded. The diameter of the reaction tube can be 0.01 to 10 meters for a length of 1 to 200 meters. It is also possible to operate several tubes in parallel. For example, a tube bundle can be employed. If a reaction tube with perforated baffle plates is used, the baffle plates are generally at a distance of from 0.1 to 5 m from one another.

When the reaction between propylene and perpropionic acid (step g) is carried out according to the invention it is possible to achieve yields of propylene oxide of more than 97%, relative to perpropionic acid employed. The amount of by-products, for example propylene glycol, propylene glycol monoester and propylene glycol diester, is less than 1 mol%, for example 0.7 mol% or less, relative to propylene oxide formed.

The reaction mixture is worked up in a manner which is in itself known. The aim of the working up is to obtain pure propylene oxide and optionally to isolate excess propylene, propionic acid and the organic solvent in a degree of purity such that it is possible to recycle these into the process.

The reaction mixture is generally worked up by distillation. It is appropriate to separate propylene oxide and propionic acid from one another very rapidly. For this purpose, for example, a distillation column is used in which propylene oxide, optionally together with lower boiling constituents and part of the solvents, is first taken off over the top and the remaining solvent and the propionic acid are obtained as the sump product. The top product is further worked up, for example in a further distillation, in order to isolate pure propylene oxide. The organic solvent (benzene) and propionic acid are recovered from the sump products from these two distillation columns. The distillation residue from the distillation of propionic acid is the small amount of high-boiling constituents, which has already been mentioned. In principle, the solvent benzene can be recovered quantitatively.

Figure 2:
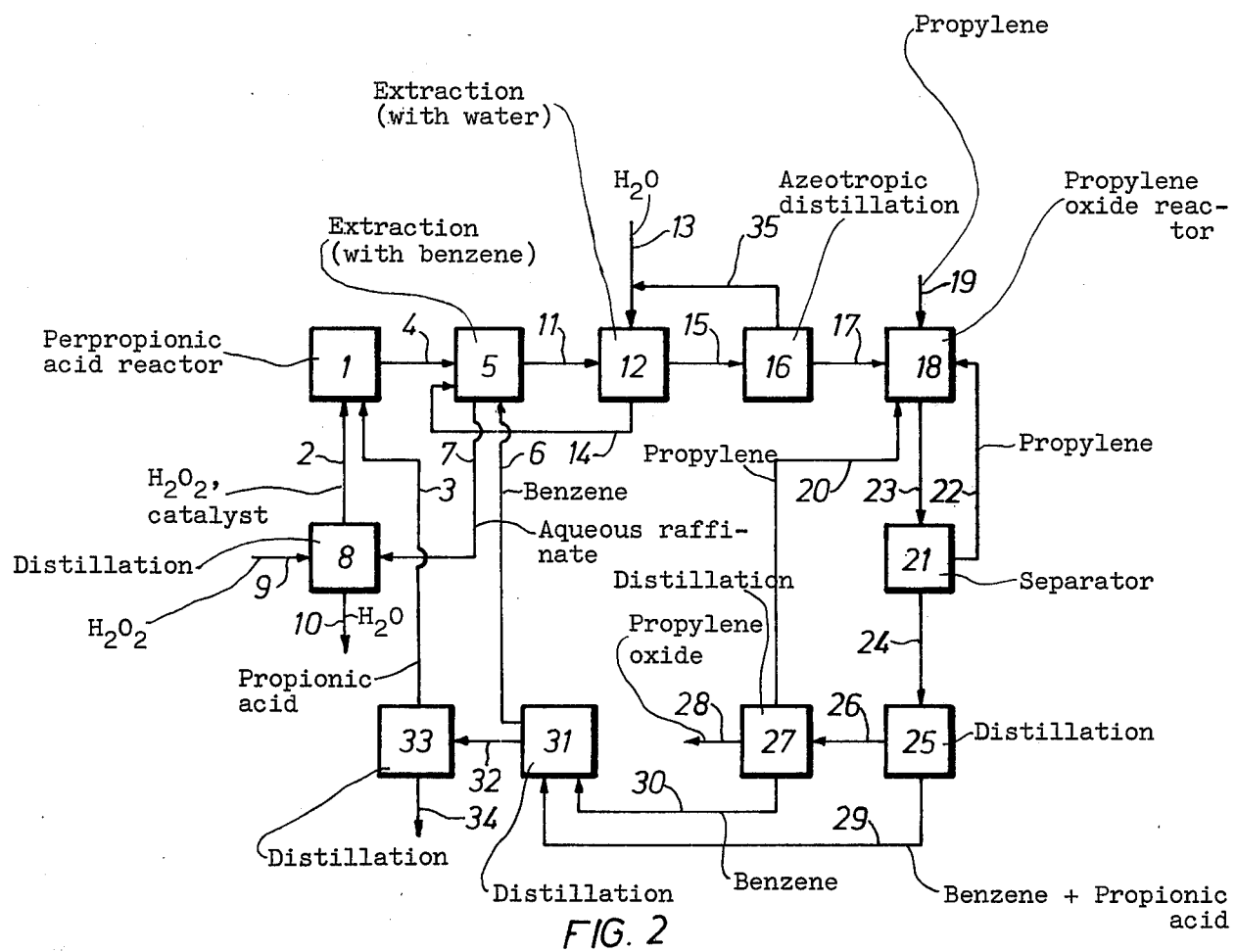
Figure 3:
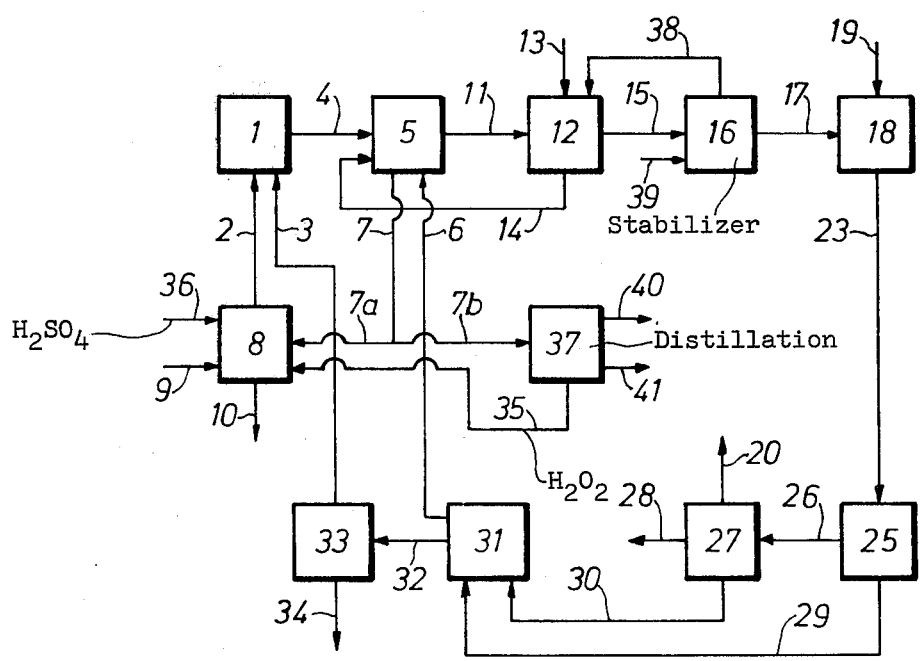

FIGS. 1, 2 and 3 depict embodiments of the process.

One embodiment of the process according to the invention is explained with the aid of FIG. 1. An aqueous solution containing 32 to 39% by weight of sulphuric acid and 28 to 32% by weight of hydrogen peroxide is fed via 2 and, at the same time, propionic acid is fed via 3, in a molar ratio of hydrogen peroxide to propionic acid of 0.9 to 1.2 : 1, at a temperature of 25° to 45° C, into the first reaction stage 1. The residence time in reaction system 1 is 10 to 30 minutes. The reaction mixture which leaves reaction system 1 via 4 contains about 26 to 32% by weight of perpropionic acid, 12 to 17% by weight of propionic acid, 17 to 21% by weight of sulphuric acid, 5 to 8% by weight of hydrogen peroxide and 2 to 5% by weight of Caro's acid. It passes into an extraction system 5, which consists of a pulsed sieve tray column with 60 to 90 sieve trays and which is charged via 6 with benzene which has a propionic acid content of less than 0.1% by weight. The raffinate from this extraction, which is withdrawn from the extraction system 5 via 7, contains the hydrogen peroxide which was not converted in reaction system 1 and the sulphuric acid. It is passed, together with approximately 50% strength commercially available aqueous hydrogen peroxide, which is fed in via 9, into the distillation unit 8, which consists of an evaporator and a column and in which, at 40–120 mm Hg and at a sump temperature of 60° to 80° C, such an amount of water is taken off over the top that an aqueous solution containing 32 to 39% by weight of sulphuric acid and 28 to 32% by weight of hydrogen peroxide is obtained as the sump product, this solution being recycled via 2 into the reaction system 1. The water taken off over the top in distillation unit 8 is withdrawn from the process via 10. The amount of water which is obtained as the distillate essentially corresponds to the amount of water which is contained in the feed hydrogen peroxide plus the amount of water which is formed in the process stage according to a, that is to say in reaction system 1. A falling flow evaporator is used as the evaporator unit for the distillation column 8. The benzene extract of perpropionic acid from extraction system 5 is passed via 11 into the extraction system 12, which consists of 3 mixer/settlers, where the extract is extracted in countercurrent with water, which is fed in via 13. The amount of water is 3 to 6 per cent by volume of the benzene solution. The aqueous phase from this extraction unit 12 is recycled via 14 into the extraction unit 5. The benzene solution of perpropionic acid which is treated with water passes via 15 into the distillation unit 16, where an azeotropic dehydration is carried out. The pressure inside distillation system 16 is 100 to 300 mm Hg. The sump temperature is 50° to 75° C. The water content of the benzene solution of perpropionic acid, which flows out of the sump of this column, is less than 0.1% by weight. The benzene solution of perpropionic acid, which is substantially anhydrous and free from hydrogen peroxide and which is obtained as the sump product from the azeotropic distillation, is fed via 17 into the reaction system 18, where the reaction with propylene takes place in a molar ratio of propylene: perpropionic acid of 1.1 to 3 : 1. The propylene passes via 19, 20 and 22 into reaction system 18. The pressure in 18 is 4 bars. The reaction system 18 consists of 2 loop reactors in series with a downstream delay tube 10 to 80 m in length. The temperature in the two loop reactors, in which the reactants are mixed by means of a circulation pump, is 50° to 80° C. 80 to 95% of the perpropionic acid are converted. The further reaction of the perpropionic acid up to a conversion of 99.8% takes place in the downstream delay tube, which is operated without cooling. The resulting reaction mixture is passed via 23 into a let-down vessel 21, where it is let down. The gas phase, thus obtainable, essentially contains propylene, Which is recycled via 22 into the reaction with perpropionic acid. Propylene oxide is next separated, together with residual propylene and with part of the benzene, by distillation from the liquid phase, which passes via 24 into the distillation unit 25. The stream containing propylene, propylene oxide and benzene is fed via 26 to the distillation unit 27, where further separation of the components takes place and pure propylene oxide is obtained, which leaves the process via 28. Propylene is recycled via 20 into the reaction system 18. The sump products from columns 25 and 27 are fed via 29 and 30 to a further distillation unit 31, where benzene is recovered as the top product and is recycled via 6 into extraction system 5. The sump product, which essentially consists of propionic acid, from the benzene recovery column 31 is fed via 32 to the distillation unit 33, in which propionic acid is distilled off as the top product, this propionic acid being recycled via 3 into the reaction system 1. The products which boil higher than propionic acid are obtained as the sump product from the distillation 33 and are withdrawn via 34.

According to the process of the invention, propylene oxide can be prepared in yields of at least 94%, relative to hydrogen peroxide employed, and of at least 97%, relative to propylene employed.

The advantages of the process according to the invention can be summarised as follows:

1. Excellent economics due to the high yields;
2. no by-products which pollute the environment, such as, for example, in the case of the chlorohydrin process;
3. no co-products such as, for example, in the case of the processes which use hydrocarbon peroxides as the oxidising agent for propylene;
4. negligible amounts of by-products, such as propylene glycol, propylene glycol monopropionate or propylene glycol dipropionate;
5. less technical effort due to simple process measures; and
6. virtually complete elimination of the explosion hazard, caused by the handling of peroxy compounds, as is required for large scale industrial processes.

EXAMPLE 1 (see also FIG. 2)

In continuous operation, 1034 g per hour of a mixture consisting of 415 g ($\triangleq$ 5.6 mols) of propionic acid and 619 g of an aqueous solution, which contains 37.8% by weight of sulphuric acid and 30.8% by weight of hydrogen peroxide ($\triangleq$ 5.6 mols of $H_2O_2$), are passed through the reaction system (1), which consists of a delay tube which can be heated, which is provided with packing and which has a length of 55 cm and a diameter of 5 cm.

In the aqueous solution containing hydrogen peroxide and sulphuric acid, part of these components are present as Caro's acid. This part amounts of 5.8% by weight, relative to the total amount of the aqueous solution, which thus has the following composition: 32.8% by weight of free sulphuric acid, 29.1% by weight of free hydrogen peroxide and 5.8% by weight of Caro's acid. The molar ratio of hydrogen peroxide to propionic acid in the mixture which passes into reaction system 1 is 1 : 1, the hydrogen peroxide bound in the Caro's acid being calculated as free $H_2O_2$.

Inside reaction system (1) the mixture, which now consists of propionic acid, sulphuric acid, hydrogen peroxide, water and Caro's acid, is warmed at 40° C for about 18 minutes, 59% of the propionic acid being converted to perpropionic acid. After passing through the delay tube, the product stream (1034 g per hour), which contains, on average, 28.8% by weight of perpropionic acid, 16.5% by weight of propionic acid, 19.6% by weight of sulphuric acid, 3.47% by weight of Caro's acid, 6.54% by weight of hydrogen peroxide and 25.1% by weight of water, is cooled to room temperature and passed into a gas separator, where 166 ml per hour of a gas consisting of 87% of oxygen and 13% of carbon dioxide are released. The degassed mixture is then fed, after it has been combined with the mixture of the two aqueous phases flowing out of the extraction unit 12, to the extraction system 5. The extraction process is carried out at a temperature of 20° C. A pulsed sieve tray column, which is provided with 80 sieve trays, which has a length of 4 m and a diameter of 25 mm and which is fitted at both the upper and the lower ends with one separating vessel in which the phase separation takes place, is used as the extraction system. The product stream which is obtained after degassing and which is combined with the mixture, fed in via line 14, of the aqueous phases from extraction system 12, is fed in at the upper end of column 5 and flows, as the heavy phase, through the column from top to bottom, whilst benzene, which serves as the extraction agent and which contains 0.09% by weight of propionic acid as well as traces of water, is fed into the column, at the lower end, in an amount of 1092 ml per hour (= 961 g/hour). 1585 ml per hour of a benzene solution of perpropionic acid ($\triangleq$ 1,490 g/hour), which, in addition to 21.4% by weight of perpropionic acid, still contains 12.6% by weight of propionic acid, 0.97% by weight of water, 0.51% by weight of hydrogen peroxide and also races of sulphuric acid, are withdrawn from the upper separating vessel.

The raffinate from the extraction collects as the heavy phase in the lower separating vessel and is removed continuously from there via line 7. This raffinate, which is obtained in an amount of about 587 g per hour, contains, on average, 34.58% by weight of sulphuric acid, 11.16% by weight of hydrogen peroxide, 6.12% by weight of Caro's acid and also 0.1% by weight of propionic acid and 0.06% by weight of perpropionic acid. This raffinate is made up for further reaction with propionic acid by treating it with 195.6 ml per hour of a 50% strength aqueous solution of hydrogen peroxide ($\triangleq$ 117 g $\triangleq$ 3.44 mols of $H_2O_2$), added via line 9, and again reconcentrating the mixture, thus obtained, by distilling off 202 g of water. This reconcentration process takes place in distillation unit 8, which is operated at a pressure of 40 mm Hg and which consists of a column (length = 1 m, diameter = 50 mm) provided with bubble cap trays, a condenser, a device which enables the reflux ratio to be varied, and a falling film evaporator, which can be heated by the vapours of a boiling liquid. The mixture, which consists of the raffinate from extraction 5 and the aqueous solution of hydrogen peroxide, is fed into the lower part of column 8. At a sump temperature of 60°-62° C, a temperature at the top of the column of 32° C and with a reflux ratio of 0.7 (reflux/take-off), 202 ml per hour of water distil over. This distillate contains traces of hydrogen peroxide as well as 0.2% by weight of perpropionic acid and 0.3% by weight of propionic acid. 619 g per hour of an aqueous solution, which in turn contains 32.8% by weight of sulphuric acid, 29.1% by weight of hydrogen peroxide and 5.8% by weight of Caro's acid, are withdrawn from the sump of the column via line 2. After it has been cooled to room temperature, this mixture is recycled into reaction system 1.

About 4.5 g per hour are withdrawn, as the raffinate from extraction 5, from the circulating stream of hydrogen peroxide and sulphuric acid, which is thus set up and which comprises the reaction system 1 and the extraction system 5 as well as the distillation unit 8. The loss of sulphuric acid, which has thus resulted in the circulation, is made up by feeding continuously the same amount per hour of a mixture, which has the composition of the raffinate from extraction 5, into the circulation before the distillation unit 8.

The loss of hydrogen peroxide which results from this exchange in the circulation is 0.5%, relative to the fresh hydrogen peroxide fed in before distillation unit 8.

The benzene solution of perpropionic acid, which is withdrawn, as the light phase, from extraction system 5, is fed via line 11 to extraction system 12, which is designed as a three-stage battery of mixer/settlers, which are arranged one above the other and each of which consists of a mixing pump with a subsequent settling vessel of about 2 liters capacity, and flows upwards through the system.

In addition to the benzene solution of perpropionic acid, 67 ml per hour of an aqueous solution, which is obtained when the aqueous phase of the top product from the subsequent azeotropic distillation (distillation unit 16), which is obtained in an amount of 60 ml per hour and which contains 1.48% by weight of $H_2O_2$, 2.43% by weight of perpropionic acid and 0.279 by weight of propionic acid, is mixed via line 35 with 7 ml of deionised water introduced via line 12, are fed to the mixing pu of the lower stage. The benzene solution, which is withdrawn as the light phase from the lower separating vessel, is fed, after passing through the middle mixer/settler arrangement, together with 17 ml/hour of fresh water to the mixing pump of the upper mixer/settler unit. The aqueous phase which is obtained here after phase separation has taken place is fed into the middle extraction stage. The aqueous solutions which collect as the heavy phase in the middle and lower separating vessels are combined and fed via 14 back into extraction unit 5 in such a way that this stream, which consists of an aqueous solution which contains 25.23% by weight of perpropionic acid, 6.8% by weight of hydrogen peroxide and 22.35% by weight of propionic acid, is mixed, in an amount of 81 ml/hour, immediately prior to entry into the pulsed sieve tray column (extraction system 5) with the product stream 4 coming from reaction system 1.

1493 g (= 1,570 ml) per hour of a benzene solution of perpropionic acid having the composition 20.04% by weight of perpropionic acid, 11.41% by weight of propionic acid, 3.95% by weight of water and 0.2% by weight of hydrogen peroxide are withdrawn as the light phase from the separating vessel of the upper mixer/settler unit of extraction system 12 via line 15 and fed into the distillation unit 16, where the solution is dried azeotropically. Before it is fed into distillation unit 16, the benzene solution of perpropionic acid is treated with 5 ml per hour of an approximately 3% strength by weight solution, in propionic acid, of a stabiliser of the type of the commercially available Na salts of partially esterified polyphosphoric acids.

The distillation unit 16 is operated at 210 mm Hg and consists of a thin layer evaporator, a 50 cm long column, 50 mm in diameter, which is provided with 5 bubble cap trays, a condenser and also a separator for phase separation of the distillate at the top of the column. The temperature in the sump of the column is 65° C. 60 ml per hour of water and about 915 ml per hour of benzene are obtained as the distillate. The benzene is returned as reflux to the column, whilst the water obtained in the separator is fed, as already described, as washing water via 35 into the lower stage of extraction unit 12. A 20.71% strength by weight benzene solution of perpropionic acid, which also contains 12.18% by weight of propionic acid as well as 0.1% by weight of water and 0.15% by weight of hydrogen peroxide, is obtained, in an amount of 1,438 g per hour, as the sump product from this azeotropic distillation.

The yield of perpropionic acid in the benzene extract dried in this way is 96.15%, relative to the hydrogen peroxide fed into the process.

The dried benzene solution of perpropionic acid, which is thus obtained, is reacted with excess propylene in a three-stage kettle cascade (reaction system 18). The reaction is carried out at a pressure of 4 bars. The propylene is fed into the first reactor in the gaseous form. The excess propylene, relative to the perpropionic acid employed in the reaction, is 170 mol% ($\triangleq$ 236 g of propylene). The first reactor of this three-stage cascade, which, like the two downstream reaction vessels, is provided with a stirring device and has a capacity of 2000 ml, is operated at a temperature of 65° C and the second and third reactors are both operated at a temperature of 70° C. The average residence time for the reaction mixture formed from the benzene solution of perpropionic acid and propylene is about 3.3 hours over the three reactors.

Under these reaction conditions, 99.8% of the perpropionic acid in the feed are converted. After the third reactor, the reaction mixture, which is obtained in an amount of 1674 g per hour and the average composition of which is 5.86% by weight of propylene, 11.31% by weight of propylene oxide, 25% by weight of propionic acid and 57.4% by weight of benzene as well as 0.15% by weight of water, is let down to normal pressure in separating vessel 21, part (78 g/hour) of the excess propylene being released as a gas.

This mixture is separated in a downstream distillation train, 189.6 g per hour of 99.9% strength pure propylene oxide being obtained. 961 g per hour of benzene and 415.9 g per hour of propionic acid are also obtained and the benzene is recycled into extraction system 5 (via line 6) and the propionic acid is recycled into reaction system 1 via line 3. In addition to propylene oxide, benzene and propionic acid, 0.38 g per hour of propylene glycol and also 3.38 g per hour of propylene glycol dipropionate are obtained when the reaction mixture is worked up by distillation and these products are passed, without further working up, to a suitable further use.

The yield of propylene oxide is thus 98.7%, relative to the perpropionic acid fed into reaction system 18, or 94.9%, relative to the hydrogen peroxide fed into reaction system 1.

The losses of propionic acid are 0.98% of the total amount fed into the process, 0.63% of this amount being contained in the propylene glycol dipropionate.

EXAMPLE 2 (see also FIG. 2)

The procedure is as in Example 1 and after the reaction mixture from reaction system 18 has been let down in separating vessel 21, a product stream of 1596 g per hour is obtained and is fed via line 24 to distillation column 25, where all of the propylene oxide, together with the propylene and part of the benzene, is withdrawn as the distillate. This distillate, which contains 3.16% by weight of propylene, 29.78% by weight of propylene oxide, 66.59% by weight of benzene and 0.4% of water and which is obtained in an amount of 636 g per hour, is fed to the distillation column 27, where 189.6 g per hour of 99.9% pure propylene oxide and 20.1 g per hour of propylene are obtained. The sump products from columns 25 and 27 are fed via line 29 and 30 respectively to column 31, where the benzene is recovered as the top product in an amount of 961 g per hour and is then recycled via line 6 into extraction system 5. The sump product from column 31 passes via line 32 into distillation column 33. Here, 415.9 g per hour of propionic acid are obtained as the top product and are recycled via line 3 into reaction system 1. 0.38 g per hour of propylene glycol and 3.38 g per hour of propylene glycol dipropionate are withdrawn from the sump of column 33.

The yield of propylene oxide and the losses of propionic acid are the same as in Example 1.

Per hour, 98.1 g (= 41.56%) of the amount of propylene (236 g) fed per hour into the reaction system 18 are recovered; the amount of propylene oxide obtained per hour contains 58.12% of the propylene. The amounts of propylene contained in propylene glycol dipropionate and in propylene glycol are 0.96 g, which corresponds to a loss of 0.41%, relative to the amount of propylene fed in per hour.

EXAMPLE 3 (see also FIG. 3)

In continuous operation, 20.12 kg ($\triangleq$ 271 mols) of propionic acid (99.8% strength by weight, stream 3) and 29.94 kg of an aqueous solution (stream 2), which contains, on average, 29.4% by weight of hydrogen peroxide ($\triangleq$ 259 mols), 33.0% by weight of sulphuric acid and 7.5% by weight of Caro's acid, are pumped per hour through the reaction system 1 which consists of a two-stage stirred kettle cascade. The molar ratio of hydrogen peroxide to propionic acid is 1.03 : 1, the hydrogen peroxide bound in the Caro's acid being calculated as free $H_2O_2$.

With an average residence time of 28 minutes in the stirred kettle cascade and at a reaction temperature of 35° C, 57.4% of the pripionic acid are converted to perpropionic acid. The reaction mixture (50.06 kg per hour, stream 4) contains, on average, 28.0% by weight of perpropionic acid, 17.1% by weight of propionic acid, 7.0% by weight of hydrogen peroxide, 19.7% by weight of sulphuric acid, 4.5% by weight of Caro's acid and 23.7% by weight of water. This reaction mixture is fed, together with the combined aqueous phases (stream 14) from the extraction unit 12, to the extraction system 5.

A pulsed sieve tray column with 60 trays, a length of 6 m and a diameter of 72 mm is used as the extraction system 5. 45.74 kg per hour of benzene (stream 6), which contains 0.11% by weight of propionic acid and 0.12% by weight of water, are fed into the column as the extraction agent.

At the upper end of the column, 74.27 kg per hour of benzene extract (stream 11), which contains, on average, 22.3% by weight of perpropionic acid, 13.8% by weight of propionic acid, 0.54% by weight of hydrogen peroxide, 0.86% by weight of water and traces of sulphuric acid, are withdrawn.

The aqueous raffinate from the extraction (stream 7) is withdrawn at the lower end of the column in an amount of 29.18 kg per hour. This raffinate contains, on average, 11.7% by weight of hydrogen peroxide, 33.8% by weight of sulphuric acid, 7.7% by weight of Caro's acid and also 0.09% by weight of perpropionic acid and 0.06% by weight of propionic acid.

A small partial stream of the raffinate (stream 7b) of 0.88 kg/hour ($\triangleq$ 3.0%) is withdrawn and worked up separately.

The bulk of the raffinate (product stream 7a), 28.3 kg/hour, is again made up for renewed reaction with propionic acid by passing it, together with 10.98 kg/hour of 50% strength aqueous hydrogen peroxide ($\triangleq$ 161.4 mol/hour of $H_2O_2$ feed, stream 9), a further 0.52 kg/hour of 17% strength by weight aqueous hydrogen peroxide (product stream 35) and 0.37 kg/hour of sulphuric acid (95.9% strength by weight, stream 36, as replacement for the loss of $H_2SO_4$ contained in stream 7b), to a distillation unit 8 and reconcentrating the mixture thus obtained by distillation off water.

The distillation unit 8 consists of packed column (length = 4m, diameter = 150 mm), a condenser and a falling film evaporator made of zirconium ("commercial grade"). The mixture of product streams 7a, 9, 35 and 36 is passed directly to the evaporator. At a pressure of 55 mm Hg, a sump temperature of 76°–78° C, a temperature at the top of the column of 38°–39° C and a reflux ratio of 0.55 (reflux/take-off), 10.21 kg per hour of water are distilled off. This distillate (stream 10) contains 0.04% by weight of hydrogen peroxide as well as 0.25% by weight of perpropionic acid and 0.16% by weight of propionic acid.

29.94 kg per hour of an aqueous solution (stream 2), which in turn contains 29.4% by weight of hydrogen peroxide, 33.0% by weight of sulphuric acid and 7.5% by weight of Caro's acid, are withdrawn from the sump of the column. After it has been cooled to 20° C, this mixture is fed back to the reaction system 1.

The raffinate partial stream 7b, 0.88 kg/hour, withdrawn from the aqueous circulation is worked up in a distillation unit 37. This consists of a packed column (length = 4 m, diameter = 100 mm), which, above the feed point located in the centre, possesses a take-off weir for withdrawing a sidestream. The column is operated at a pressure of 50 mm Hg, a temperature at the top of 38° C and a reflux ratio of 0.1.

5.5 kg of steam per hour are blown in above the sump. 0.52 kg per hour of 17% strength by weight aqueous hydrogen peroxide are withdrawn from the column as a sidestream (product stream 35) and fed to the distillation unit 8. In addition, 4.96 kg/hour of water with 0.04% by weight of hydrogen peroxide (stream 40) are obtained as the distillate and 0.90 kg/hour of an aqueous solution (stream 41), which contains 1.2% by weight of hydrogen peroxide, 34.7% by weight of sulphuric acid and 5.6% by weight of Caro's acid, are obtained in the sump.

The benzene extract (stream 11) withdrawn from the extraction column 5 is passed to a further extraction system 12, which is designed as a three-stage battery of mixer/settlers arranged in one plane and each consisting of a mixing pump followed by a separator.

The benzene extract (stream 11), together with 0.78 kg/hour of fresh water (stream 13) and 2.92 kg/hour of the aqueous phase (stream 38) from the azeotropic distillation 16, is fed to the mixing pump of the first stage. The benzene solution, which is withdrawn from the first separator as the light phase, is fed, after passing through the second mixer/settler unit, together with 0.93 kg/hour of fresh water to the mixing pump of the third stage. The aqueous phase separated off in this stage is fed into the second stage.

The aqueous phases obtained in the first stage and the second stage are combined (product stream 14) and passed back, in an amount of 7.65 kg/hour, into the extraction column 5. These combined aqueous phases contain, on average, 3.8% by weight of hydrogen peroxide, 33.7% by weight of perpropionic acid, 21.8% by weight of propionic acid, 10.0% by weight of benzene and a little sulphuric acid. 71.25 kg per hour of a benzene solution (stream 15), which contain, on average, 19.7% by weight of perpropionic acid, 12.1% by weight of propionic acid, 0.19% by weight of hydrogen peroxide and 4.0% by weight of water, are withdrawn, as the light phase, from the separator of the third stage and fed, together with a solution of a stabiliser, to the azeotropic distillation 16.

A commercially available Na salt of a partially esterified polyphosphoric acid is used as the stabilizer and is added as a 15% strength by weight solution in propionic acid (0.11 kg/hour, stream 39).

The distillation unit 16 consists of a packed column (length = 3 m, diameter = 200 mm), a falling film evaporator, a condenser and a separator for phase separation of the distillate at the top of the column. The product stream 15 is fed into the lower part of the column. At a pressure of 300 mm Hg and a temperature at the top of the column of 46°–48° C, 2.92 kg of aqueous phase and about 54 kg of benzene phase are obtained per hour as the distillate. The benzene phase is returned to the column as reflux, whilst the aqueous phase (product stream 38) which contains 0.82% by weight of hydrogen peroxide, 1.10% by weight of perpropionic acid and 0.34% by weight of propionic acid, is passed into the first stage of the extraction system 12.

68.25 kg per hour of a benzene solution of perpropionic acid (20.49% by weight $\triangleq$ 155.2 mols), which also contains 12.67% by weight of propionic acid, 0.16% by weight of hydrogen peroxide, less than 0.1% by weight of water and the abovementioned stabiliser, (stream 17) are obtained as the sump product from this azeotropic distillation.

The yield of perpropionic acid in the dried benzene solution is 96.1%, relative to the amount of hydrogen peroxide fed into the process (stream 9).

The dried benzene solution of perpropionic acid, thus obtained, (stream 17) is reacted with 7.4 kg/hour of very pure propylene ($\triangleq$ 175.8 mols/hour, product stream 19) in reaction system 18. The excess propylene, relative to the feed perpropionic acid, is 13.3 mol%.

Reaction system 18 consists of two loop reactors in series with a downstream delay tube. The reaction is carried out at a pressure of 4 bars. All of the propylene is fed into the first loop reactor. The reaction temperature is 65° C in the two loop reactors and the average residence time of the reaction mixture is about 45 minutes in each. In the delay tube, the reaction temperature is 70° C and the average residence time of the reaction mixture is about 70 minutes. About 90% of the perpropionic acid has been converted at the exit from the second loop reactor and after the delay tube a conversion of 99.8% is achieved. The reaction mixture then contains, on average, 1.16% by weight of propylene, 11.8% by weight of propylene oxide, 60.1% by weight of benzene and 26.5% by weight of propionic acid.

This reaction mixture (product stream 23) is let down in separator 21 and then enters the distillation column 25, in which propylene, all of the propylene oxide and part of the benzene are separated off as the distillate (stream 26).

This distillate, which contains, on average, 5.4% by weight of propylene, 62.5% by weight of propylene oxide and 31.2% by weight of benzene, is fed into the distillation column 27. 0.73 kg of propylene (stream 20) and 8.91 kg of propylene oxide (99.9% pure, stream 28) are withdrawn per hour from this column. After separating an aqueous phase, which contains 0.01 kg/hour of free propylene glycol, from the product withdrawn from the sump of column 27, this sump product (stream 30) is fed, together with the sump product withdrawn from column 25 - stream 29 - into the distillation column 31. 45.48 kg per hour of benzene are obtained as the distillate from this column and are recycled, with 0.26 kg/hour of fresh benzene (loss replenishment), as stream 6 to the extraction column 5. The product (stream 32) withdrawn from the sump of distillation column 31 is fed to distillation column 33. 19.91 kg per hour of propionic acid are obtained as the distillate from this column and are recycled, with 0.21 kg/hour of fresh propionic acid (loss replenishment), as product stream 3 into reaction system 1. 0.21 kg per hour of propylene glycol dipropionate (stream 34) are withdrawn from the sump of column 33.

The yield of propylene oxide is 98.7% relative to the perpropionic acid fed into reaction system 18, and 94.9%, relative to the hydrogen peroxide employed (product stream 9). The losses of propylene are 3% (0.7% of which is in the byproducts propylene glycol and propylene glycol dipropionate). The losses of benzene are 0.57% and those of propionic acid are 1.49%, 0.81% of which is contained in the propylene glycol dipropionate.

Figure 4:
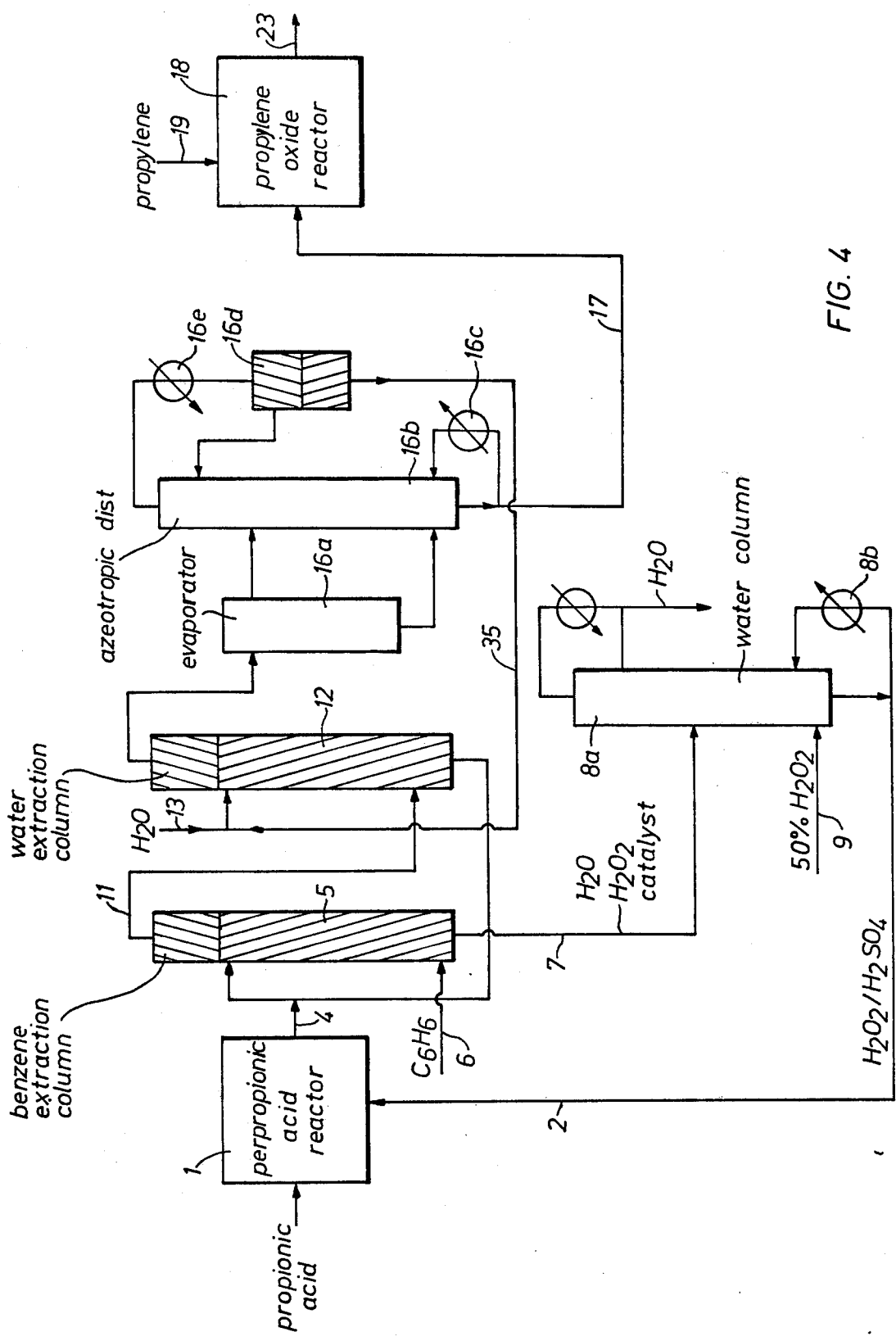

EXAMPLE 4 (see also FIG. 4)

An aqueous perpropionic acid solution is produced in reactor 1. Therein 50% aqueous $H_2O_2$ and propionic acid are reacted in a ratio of 0.8 to 1.2 : 1 in the presence of 22% $H_2SO_4$ as the catalyst at a pressure of 1 bar and a temperature of 32°-36° C. A mixture of the following composition is produced:

| | |
|---|---|
| perpropionic acid | 30% |
| propionic acid | 15% |
| $H_2SO_4$ | 22% |
| $H_2O$ | 25.8% |
| $H_2O_2$ | 7.2% |

Perpropionic acid and propionic acid are then taken up by benzene in benzene extraction column 5.

Benzene is introduced in counterflow into extractor 5, into which the aqueous solution obtained from reactor 1 is introduced via line 4. A pressure 1 bar and a temperature of 20°-50° C prevails in the extractor 5. A benzene and an aqueous phase of the following compositions are produced:

| benzene phase: | perpropionic acid | 23% |
|---|---|---|
| | propionic acid | 13.3% |
| | $H_2O$ | 1% |
| | $H_2O_2$ | 0.5% |
| | benzene | remainder |

| aqueous phase: | $H_2SO_4$ | 35% |
|---|---|---|
| | $H_2O_2$ | 11.3% |
| | $H_2O$ | remainder |

$H_2O_2$ is then removed from the benzene-perpropionic acid solution in extractor 12.

The benzene phase obtained from extractor 5 is extracted with 1-5% fresh $H_2O$ introduced via line 13 in countercurrent flow. The conditions are the same as in extractor 5. A benzene phase and an aqueous phase of the following compositions are formed:

| benzene phase: | perpropionic acid | 20% |
|---|---|---|
| | propionic acid | 12% |
| | $H_2O$ | 4.2% |
| | $H_2O_2$ | less than 0.05% |

| aqueous phase: | perpropionic acid | 36% |
|---|---|---|
| | $H_2O$ | 25% |
| | propionic acid | 20% |
| | $H_2O_2$ | 6% |

The aqueous phase is recycled to extractor 5.
The benzene-perpropionic solution is then dried.
The benzene solution obtained from column 12 is fed into falling film evaporator 16a with short residence time. The resulting vapour phase is conducted to about the middle and the liquid phase to the bottom of a drying column 16b which is supplied with benzene vapours from below. The falling film evaporator 16a and the drying column are operated at a pressure of 250 mm Hg and a temperature of 50°-70° C. From the head of the drying column a $C_6H_6/H_2O$ azeotrope is withdrawn and forms two phases in separator 16d after cooling in cooler 16e. The aqueous phase is recycled to extractor 12 via 35; the benzene phase is conveyed as reflux to the head of the drying column.

From the sump of the drying column, a benzene solution is removed via line 17 which contains 20% perpropionic acid and 10% propionic acid and is practically free of $H_2O$ and $H_2O_2$.

The aqueous phase from benzene extraction column 5 is worked up as follows.

The aqueous phase in line 7 is fed via line 7a into the center part of the water column 8a which is operated at a sump temperature of 60°-90° C and a pressure of 50-100 mm Hg. All the fresh 50%-strength, aqueous $H_2O_2$ required in the propionic acid reaction 1 is introduced into the lower part of the water column via line 9. The sump product which consists of $H_2O$, $H_2O_2$ and $H_2SO_4$ is in part conveyed via line 2 to propionic acid reaction 1, and is in part past through heater 8b. Water vapour which may contain traces of $H_2O_2$ is removed at the head of water column 8a.

The reaction of the benzene-perpropionic acid solution with propylene is performed in propylene oxide reactor 18. The benzene solution from azeotropic distillation column 16b, which contains about 20% perpropionic acid and 12% propionic acid is introduced into reactor 18 via line 17, as is also 1.5 to 3.0 times the molar amount of propylene (based on perpropionic acid) via line 19. The propylene introduced into reactor 18, which may contain propane, dissolves in the reaction mixture without forming bubbles so that the reaction takes place homogeneously. The reaction is conducted in such a manner that the perpropionic acid is almost completely reacted. The concentration of perpropionic acid in the reactor outlet 23 is less than 0.1% by weight. The mean residence time is 1-2 hours.

A plurality of series-connected reactor units are provided with which to perform the reaction. Reactor 18 can be as is described with reference to FIG. 3. 90% of the reaction takes place in the two loop reactors and 10% in the residence or delay pipe. The temperature in the reaction system can be about 70° C and the pressure about 6.5 bars. The product leaving the reactor is free of perpropionic acid and has roughly the following composition:

| | |
|---|---|
| $C_6H_6$ | 55% |
| propionic acid | 30% |
| propylene oxide | 12% |
| propylene + propane | 2% |

The product of reactor 18 is then worked-up in the same way as described in the foregoing examples.

What is claimed is:

1. Process for the continuous production of propylene oxide from propylene and aqueous hydrogen peroxide which comprises:
   (a) contacting aqueous hydrogen peroxide with propionic acid for reaction of hydrogen peroxide and propionic acid to form perpropionic acid, in the presence of a water-soluble acid catalyst for the reaction, the amount of water, catalyst and hydrogen peroxide corresponding to an aqueous solution of catalyst and hydrogen peroxide containing 15 to 45% by weight of catalyst and 25 to 35% by weight of hydrogen peroxide, and the molar ratio of hydrogen peroxide to propionic acid being 0.8 to 1.5 at a temperature of 10° to 70° C.
   (b) extracting the resulting reaction mixture with benzene for formation of a benzene phase rich in perpropionic acid, propionic acid, and containing hydrogen peroxide, and an aqueous raffinate phase rich in hydrogen peroxide and catalyst.
   (c) treating the aqueous raffinate to remove water therefrom and form a concentrated solution of hydrogen peroxide and catalyst.
   (d) recycling said concentrated solution of hydrogen peroxide and catalyst to step (a),
   (e) extracting the benzene phase of step (b) with water or an aqueous solution for formation of a benzene phase containing perpropionic acid, propionic acid, water and a reduced amount of hydrogen peroxide, and an aqueous phase containing hydrogen peroxide.
   (f) subjecting the benzene phase produced in step (e) to azeotropic distillation to reduce the water content thereof to less than 0.5% by weight.
   (g) contacting the benzene phase of reduced water content of step (f) with propylene at a temperature of 40° to 100° C and a pressure of 2 to 30 bars for reaction of perpropionic acid of the benzene phase with propylene to form propylene oxide and reaction mixture containing the propylene oxide, and other materials,
   (h) distilling the reaction mixture is distill overhead propylene, propylene oxide and benzene and removing bottoms comprising benzene and propionic acid;
   (i) subjecting the overhead from step (h) to a second distillation to distill off overhead propylene and recycling said propylene to step (g);
   (j) introducing the bottoms consisting essentially of propionic acid and benzene from the distillation of step (i) to a third distillation and distilling off overhead benzene and recycling said benzene to step (b),
   (k) removing bottoms from said third distillation consisting essentially of propionic acid and materials of higher boiling point than propionic acid and introducing said bottoms into a fourth distillation and distilling over propionic acid and recycling said propionic acid to step (a) and separating bottoms consisting essentially of the material of higher boiling point than propionic acid, and
   (l) recovering propylene oxide as a side cut from said second distillation.

2. Process of claim 1, wherein the water-soluble acid catalyst in step (a) is sulfuric acid.

3. Process of claim 2, wherein, in step (a), the amount of water catalyst and hydrogen peroxide corresponds to an aqueous solution of catalyst and hydrogen peroxide of 34 to 39% by weight of catalyst and 28 to 32% by weight of hydrogen peroxide.

4. Process of claim 1, wherein, in step (a), the molar ratio of $H_2O_2$: propionic acid is 0.9 to 1.3 : 1.

5. Process of claim 1, wherein, in step (a), the temperature is 20° to 60° C.

6. Process of claim 1, wherein, in step (a), the temperature is 30° to 40° C.

7. Process of claim 1, wherein, in step (b), the ratio of benzene to the reaction mixture is 0.3 to 3:1.

8. Process of claim 1, wherein, in step (b) the benzene used for the extraction contains less than 0.5 percent of propionic acid.

9. Process of claim 1, wherein, in step (b), the temperature is 10° to 70° C.

10. Process of claim 1, wherein, in step (c), the aqueous raffinate is distilled to remove water therefrom at 50 to 150 mm Hg and at a temperature of 60° to 85° C.

11. Process of claim 1, wherein, in step (c), the aqueous raffinate is distilled to remove therefrom water containing less than 0.1 percent by weight of hydrogen peroxide.

12. Process of claim 1, wherein 0.1 to 6% by weight of the aqueous raffinate of step (b) is withdrawn.

13. Process of claim 12, wherein the withdrawn aqueous raffinate contains hydrogen peroxide and sulfuric acid, and is regenerated for recovery of hydrogen peroxide and sulfuric acid.

14. Process of claim 13, wherein the hydrogen peroxide and sulfuric acid recovered in said regeneration is recycled for use in step (a).

15. Process of claim 1, wherein the benzene phase subjected to extraction in step (e) contains 15 to 25% by weight perpropionic acid.

16. Process of claim 1, wherein, in step (e), the amount of water used for extraction of the benzene extract is 3 to 6 percent by volume of the benzene phase subjected to the extraction.

17. Process of claim 1, wherein an aqueous phase is formed in the azeotropic distillation of (f), and the aqueous phase of step (f) is used in step (e) to provide water for the extraction of step (e).

18. Process of claim 1, wherein the aqueous phase containing hydrogen peroxide produced in step (e) is recycled to step (b).

19. Process of claim 1, wherein, in step (f), the temperature of the azeotropic distillation is 30° to 80° C, and the pressure is 200 to 400 mm hg.

20. Process according to claim 1, wherein, in step (f), the water content of the benzene phase is reduced to less than 0.2% by weight.

21. Process of claim 1, wherein, in step (g), the molar proportion of propylene: perpropionic acid subjected to said contacint is 1.01 to 8:1.

22. Process of claim 1, wherein, in step (g), the temperature is 60° to 80° C.

23. Process of claim 1, wherein, in step (g), the molar proportion of propylene: perpropionic acid subjected to said contacting is 2 to 3:1.

24. Process of claim 1, wherein, in step (g), the contacting is performed in a reaction system which acts as a cascade of 10 to 30 ideally mixed kettles.

25. Process according to claim 1, wherein in step (g), the contacting is performed in said reaction system which acts as a cascade of 3 to 6 kettle reactors.

26. Process of claim 1, wherein, in step (g), said contacting is performed at least partially in a tubular reactor.

27. Process of claim 1, wherein, in step (g), said contacting is partially carried out in a delay tube fitted with perforated baffle plates.

28. Process of claim 1, wherein at least 50% by weight of the hydrogen peroxide introduced into step (a) is added to the aqueous raffinate introduced into step (c).

29. Process of claim 28, wherein 50 to 75% by weight of the hydrogen peroxide introduced into step (a) is added to the aqueous raffinate introduced into step (c).

30. Process of claim 28, wherein 75 to 95% by weight of the hydrogen peroxide introduced into step (a) is added to the aqueous raffinate introduced into step (c).

31. Process of claim 28, wherein all of the hydrogen peroxide introduced into step (a) is added to the aqueous raffinate introduced into step (c).

32. Process of claim 1, wherein in step (b), said reaction mixture and benzene are countercurrently contacted; in step (c) the treatment is by distillation; in step (g) an excess of propylene is used.

* * * * *

UNITED STATES PATENT AND TRADEMARK OFFICE
CERTIFICATE OF CORRECTION

PATENT NO. : 4,113,747
DATED : September 12, 1978
INVENTOR(S) : Prescher et al.

It is certified that error appears in the above-identified patent and that said Letters Patent are hereby corrected as shown below:

Column 2, line 29, first line of formula, "R-COOH" should read -- R-COOOH --.

Column 2, line 30, second line of formula, "R-COOH" first occurrence should read -- R-COOOH --.

Column 6, line 6, after "proposed" insert -- process --.

Signed and Sealed this

Twenty-third Day of January 1979

[SEAL]

Attest:

RUTH C. MASON
Attesting Officer

DONALD W. BANNER
Commissioner of Patents and Trademarks